US005602288A

United States Patent [19]
Rao

[11] Patent Number: 5,602,288
[45] Date of Patent: Feb. 11, 1997

[54] CATALYTIC PROCESS FOR PRODUCING $CF_3CH_2F$

[75] Inventor: V. N. Mallikarjuna Rao, Wilmington, Del.

[73] Assignee: E. I. Du Pont de Nemours and Company, Wilmington, Del.

[21] Appl. No.: 891,390

[22] Filed: May 29, 1992

[51] Int. Cl.[6] ................................................. C07C 19/08
[52] U.S. Cl. ........................................ 570/176; 570/123
[58] Field of Search ................................ 510/176, 123

[56] References Cited

U.S. PATENT DOCUMENTS

| | | |
|---|---|---|
| 2,644,845 | 7/1953 | Mc Bee . |
| 4,490,534 | 12/1984 | Fujikawa et al. . |
| 4,996,379 | 2/1991 | Oshio et al. . |
| 5,120,883 | 6/1992 | Rao et al. . |
| 5,136,113 | 8/1992 | Rao .................................. 570/176 |

FOREIGN PATENT DOCUMENTS

| | | |
|---|---|---|
| 1225956 | 1/1969 | Great Britain . |
| 1578933 | 5/1977 | Great Britain . |
| 358946 | 3/1991 | Japan . |

OTHER PUBLICATIONS

Chem. Abst. 87(10) 68874q.
A. A. Goleva et al., Russ. J. Phys. Chem., 44[2], 290–1 (1970).
M. Biswas et al., J. Macromol. Sci., Chem., A20 (8), 861–876 (1983).
Chem. Abst. 80(25) 145470q.
Chem. Abst. 80(25) 145469w.
Organic Synthesis, Collective vol. 3 pp. 685–690.
J. W. Hassler, "Activated Carbon", pp. 344–345.
M. Smisek et al., "Active Carbon", pp. 61–70.
F. J. Long et al., "The Effect of Specific Catalysts on the Reactions of the Steam–Carbon System", Proc. Roy. Soc. (1952) pp. 100–110.
R. B. Anderson et al., "Surface Complexes on Charcoal", J. Phys. Colloid Chem., 51, pp. 1308–1329.
H. M. Frey, "A New Type of Catalytic Effect in the Oxidation of Carbon", Proc. Roy. Soc. (1055), pp. 510–518.
A. Blackburn et al., "Adsorption from Binary Liquid Mixtures: Some Effects of Ash in Commercial Charcoal" J. Chem. Soc. (1955), pp. 4103–4106.
F. J. Long et al., "The Catalysts of the Oxidation of Carbon", J. Chem. Phys., 47, pp. 361–378 (1950).

*Primary Examiner*—Alan Siegel

[57] ABSTRACT

A process is disclosed for producing $CF_3CH_2F$ from $CF_3CHClF$ by catalytic chlorination of $CF_3CHClF$ to $CF_3CCl_2F$ at elevated temperature, and reaction of $CF_3CCl_2F$ with $H_2$ in the presence of a carbon-supported precious metal catalyst at a temperature of from about 100° C. to 250° C. Suitable catalysts for the chlorination include carbon catalysts and catalysts wherein halides of certain metals (La, Zn, Cu, Cr, Ru, Rh, and/or Pt) are supported on carbon.

19 Claims, No Drawings

CATALYTIC PROCESS FOR PRODUCING CF₃CH₂F

FIELD OF THE INVENTION

This invention relates to the chlorination of aliphatic hydrofluorocarbons and hydrochlorofluorocarbons and more particularly to catalytic chlorination of hydrofluorocarbons and hydrochlorofluorocarbons.

BACKGROUND

British Patent Specification 1,225,956 discloses a process for the production of a chlorofluoroethane of the general formula $CH_{3-n}Cl_nCClF_2$ where n is 0 to 3 comprising the photochemical chlorination of 1,1-difluoroethane, which may contain less than 2% HF.

There has been considerable interest in processes for the chlorination of aliphatic hydrofluorocarbons and hydrochlorofluorocarbons which avoid using expensive actinic light to effect such chlorination.

U.S. Pat. No. 4,490,534 discloses a process for the preparation of 3-chloro-5-trifluoromethylpyridine derivatives comprising reacting a 5-trifluoromethylpyridine having a hydrogen atom at the 3-position with chlorine in the presence of a catalyst selected from the group consisting of activated carbon and a chloride of a metal selected from the group consisting of iron, antimony, copper and zinc.

2-Chloro-1,1,1,2-tetrafluoroethane (i.e., HCFC-124 or $CF_3CHClF$) is a chlorofluoroethane which has been prepared by the addition of HF to halogenated olefins and by the reaction of 2,2-dichloro-1,1,1-trifluoroethane with HF. HCFC-124 can be reacted with hydrogen to form 1,1,1,2-tetrafluoroethane (i.e., HFC-134a or $CF_3CH_2F$) which is a useful refrigerant and propellant.

Other processes have been disclosed for the preparation of HFC-134a which can produce HCFC-124 as a by-product. For example, 2,2-dichloro-1,1,1,2-tetrafluoroethane (i.e., CFC-114a or $CCl_2FCF_3$) can be converted to HFC-134a as the major product and HCFC-124 as a minor product, by catalytic hydrogenolysis. The HCFC-124 can be recycled to the hydrogenolysis reactor to produce additional HFC-134a.

A higher temperature is generally required to catalytically hydrogenolyze HCFC-124 to HFC-134a than is required for the hydrogenolysis of CFC-114a to HFC-134a. Consequently, catalyst stability can be affected and unwanted by-products such as 1,1,1-trifluoroethane may increase. There is thus a desire to provide a means to convert HCFC-124 to HFC-134a without subjecting hydrogenolysis catalysts to such higher temperatures.

SUMMARY OF THE INVENTION

The present invention provides a process for producing 1,1,1,2-tetrafluoroethane from 2-chloro-1,1,1,2-tetrafluoroethane comprising the steps of contacting a gaseous mixture containing said 2-chloro-1,1,1,2-tetrafluoroethane and chlorine with a catalyst at a temperature of from about 225° C. to about 450° C. to produce 2,2-dichloro-1,1,1,2-tetrafluoroethane (the chlorination catalyst being selected from the group consisting of carbon catalysts and catalysts of a metal halide supported on carbon wherein the metal halide is selected from the group consisting of lanthanum chloride, lanthanum fluoride, zinc chloride, zinc fluoride, copper chloride, copper fluoride, chromium chloride, chromium fluoride, ruthenium chloride, ruthenium fluoride, rhodium chloride, rhodium fluoride, platinum chloride, platinum fluoride, and mixtures thereof) and reacting said 2,2-dichloro-1,1,1,2-tetrafluoroethane with hydrogen in the presence of a carbon-supported precious metal catalyst at a temperature of from about 100° C. to 250° C. to produce 1,1,1,2-tetrafluoroethane. The invention further provides a process for the manufacture of $CF_3CH_2F$ by reacting $CF_3CCl_2F$ with hydrogen wherein $CF_3CHClF$ is produced as a by-product, characterized by comprising the steps of contacting a gaseous mixture containing chlorine and said by-product $CF_3CHClF$ with a chlorination catalyst selected from the group described above at a temperature of from about 225° C. to 450° C. to produce $CF_3CCl_2F$; recycling the $CF_3CCl_2F$ produced by said chlorination for reaction with hydrogen; and reacting $CF_3CCl_2F$ with hydrogen in the presence of a carbon-supported precious metal catalyst at a temperature of from about 100° C. to 250° C.

DETAILS OF THE INVENTION

The present invention provides a process for the production of HFC-134a from HCFC-124 by first converting the HCFC-124 to CFC-114a by catalytic chlorination. Preferably, the HCFC-124 is converted to 2,2-dichloro-1,1,1,2-tetrafluoroethane without isomerization or disproportionation. HFC-134a may then be produced from CFC-114a using known hydrogenolysis reactions such as those described in GB 1,587,983 and U.S. Pat. No. 4,996,379. Typically some $CHClFCF_3$ (HCFC-124) is produced along with the desired $CH_2FCF_3$ (HFC-134a). In accordance with this invention, by-product HCFC-124 can be converted to CFC-114a which can be recycled for hydrogenolysis to HFC-134a.

The catalyst for the chlorination may be composed of carbon catalysts (e.g., activated carbon) alone or carbon with a chloride and/or fluoride of a metal selected from the group consisting of lanthanum, zinc, copper, chromium, ruthenium, rhodium, platinum and mixtures thereof. Under reaction conditions the metal halides may be in the form of mixed metal halides (e.g., a chlorofluoride).

Catalyst compositions consisting essentially of carbon are preferred and are considered particularly effective for chlorination. The carbon can be either washed or unwashed. Washing can be done with either water or acid. Washing, particularly with acids, reduces the ash content. Preferred acid-washed carbons contain 0.5 percent by weight or less, ash. Examples of acids which may be used in an acid wash include organic acids (e.g., acetic acid) and inorganic acids (e.g, HCl or $HNO_3$). Preferably hydrochloric acid or nitric acid is used. The acid treatment may be accomplished in several ways. A preferred embodiment is described as follows.

An activated carbon is soaked overnight with gentle stirring in a 1M solution of the acid prepared in deionized water. The carbon support is separated and washed with deionized water until the pH of the washings is about 3. The carbon support is then soaked again with gentle stirring in a 1M solution of the acid prepared in deionized water for about 12 to 24 hours. The carbon support is then finally washed with deionized water until the washings are substantially free of the anion of the acid (e.g., $Cl^-$ or $NO_3^-$), when tested by standard procedures. The carbon support is then separated and dried at about 120° C. A sample of this washed carbon is then soaked, if desired, in 1M HF prepared in deionized water for about 48 hours at room temperature with occasional stirring in an HF resistant container. The carbon support is separated and washed repeatedly with deionized water until the pH of the washings is greater than 4. The carbon support is then dried at about 150° C. followed by calcination at about 300° C. prior to its use.

Commercially available carbons useful in the process of this invention include those sold under the following trademarks: Darco™, Nuchar™, Columbia SBV™, Columbia MBV™, Columbia MBQ™, Columbia JXC™, Columbia CXC™, Calgon PCB™, and Barnaby Cheny NB™. Preferred carbons include those prepared from plant-based materials that have been twice treated with acid, as described above, to reduce the ash content. The carbon support can be in various forms (e.g., powder, granules, or pellets).

If the catalyst composition contains one or more metals selected from lanthanum, zinc, copper, chromium, ruthenium, rhodium and platinum, the percentage of metal in the catalyst composition is not considered critical. Typically, the metal content is from about 0.1% to 30% by weight of the carbon.

In accordance with this invention, gaseous $CHClFCF_3$ and chlorine is contacted with the catalyst at elevated temperature to produce $CCl_2FCF_3$. An inert diluent such as argon, helium, nitrogen or $CCl_2FCF_3$ may be used in the chlorination reaction of the present invention. HF may also be present, particularly where catalysts consisting essentially of carbon are used. The amount of chlorine is not critical but is usually from 0.5 to 10 moles, preferably from 2 to 3 moles, per mole of $CHClFCF_3$ starting material. The reaction temperature can range from 225° C. to 450° C., and is preferably from about 250° C. to 400° C. The contact time preferably ranges from about 5 to 60 seconds, and is typically about 30 seconds. Although the chlorination reaction of the present invention is usually conducted at atmospheric pressure, it may also be conducted under elevated or reduced pressure.

The chlorination reaction of the organic starting material may be conducted in any suitable reactor, such as a fixed bed reactor. It may be done in a batch or continuous mode. The reaction vessel should be constructed of materials which are resistant to the corrosive effects of hydrogen fluoride, hydrogen chloride and chlorine, such as Hastelloy® nickel alloy and Inconel® nickel alloy.

A gaseous mixture discharged from the chlorination reactor typically contains 2,2-dichloro-1,1,1,2tetrafluoroethane, unreacted starting material, hydrogen chloride, chlorine and in some cases disproportionation product(s) and/or an inert diluent. HF may be present in some embodiments of the invention. The mixture may be refined using conventional means to obtain 2,2-dichloro-1,1,1,2-tetrafluoroethane. The recovered unreacted starting material can be recycled to the reaction zone to improve the yield of 2,2-dichloro-1,1,1,2-tetrafluoroethane and in turn also improve the yield of CFC-114a hydrogenolysis to HFC-134a.

The hydrogenolysis of CFC-114a in accordance with the invention may be accomplished at temperatures of about 250° C., or less, in the presence of carbon-supported precious metal catalysts. Examples of such catalysts include palladium, platinum, and/or ruthenium supported on carbon. Carbon-supported alloys of these metals (e.g., with copper, silver, and/or gold) may also be used. Generally, temperatures from about 100° C. to 250° C. are suitable. A preferred temperature for hydrogenolysis is from about 150° to 225° C.

The invention may be integrated into a process for the manufacture of $CF_3CH_2F$ by reacting $CF_3CCl_2F$ with hydrogen wherein $CF_3CHClF$ is produced as a by-product, particularly where the hydrogenolysis is accomplished in the presence of a carbon-supported precious metal catalyst. In accordance with this invention, said by-product $CF_3CHClF$ may be chlorinated as indicated above to produce $CF_3CCl_2F$ (rather than, for example, directly reacting said $CF_3CHClF$ with hydrogen); and the $CF_3CCl_2F$ produced by chlorination of $CF_3CHClF$ by-product may be recycled for reaction with hydrogen. Accordingly, the hydrogenolysis may be conducted in the presence of a carbon-supported precious metal catalyst at a temperature of from about 100° C. to 250° C. (and preferably from about 150° to 225° C.).

Practice of the invention will become further apparent from the following non-limiting Examples.

EXAMPLES

In the following illustrative examples, all parts are by weight, all percentages are molar, and all temperatures are degrees Celsius unless otherwise stated.

General Procedure for Chlorination

The reactor (a 0.5" (about 1.3 cm) ID, 12" (about 0.5 cm) long Inconel® nickel alloy pipe) was charged with the amount of catalyst as described in the following examples, and placed in a sand bath. The catalysts were treated and activated as described in the Examples.

The reactor effluent was sampled on-line with a Hewlett Packard HP 5890 gas chromatograph using a 20' (about 6.1 m) long, ⅛" (about 0.32 cm) diameter, column containing Krytox™ perfluorinated polyether on an inert support and a helium flow of 35 cc/minute. Gas chromatographic conditions were 70° C. for 3 min followed by temperature programming to 180° C. at a rate of 6° C./minute.

Example 1

Chlorination Using HCl Washed Carbon Catalyst

A commercially available carbon (102.5 g, 4×10 mesh (about 4.8×2.0 mm) granules) was soaked overnight with gentle stirring in 1M HCl. The carbon granules were collected on a fritted glass funnel, washed with deionized water and dried on the fritted glass funnel. The carbon granules were soaked a second time in 1M HCl overnight, followed by washing with deionized water and drying on the fritted glass funnel. After a third soaking in 1M HCl overnight the carbon granules were washed with deionized water until the washings were chloride free when tested with silver nitrate. The carbon granules were then dried at 110° C. for 18 hours, followed by calcination at 300° C. in air to obtain 94.7 g of dried calcined granules.

The general chlorination procedure described above was followed using the acid washed carbon. The dried, acid-washed carbon catalyst (12.52 g, 30 ml of 4×10 mesh (about 4.8×2.0 mm) granules) was placed in the reactor and heated under a nitrogen flow to 350° C. over 1.5 hours. The temperature was reduced to 275° C. and the flow of chlorine started. After a half hour, the flow of $CF_3CHClF$ (HCFC-124) was also started. Samples were taken at various times. The molar ratio of chlorine to HCFC-124 was 3:1 for the 3 hour sample, 2:1 for the 1 hour, 2 hour, and 4.5 hour samples and 1:1 for the 3.5 hour and 4 hour samples. The contact time was 30 seconds for all the samples. The reactor effluent was analyzed as described above. The results are shown in Table 1.

TABLE 1

| Time (hr) | Temp. (°C.) | %124[1] | %114a[2] |
|---|---|---|---|
| 1.0 | 275 | 24.3 | 75.6 |
| 2.0 | 300 | 4.4 | 95.5 |
| 3.0 | 300 | 2.9 | 96.9 |
| 3.5 | 300 | 12.7 | 87.2 |
| 4.0 | 325 | 3.2 | 96.6 |
| 4.5 | 325 | 0.3 | 99.5 |

[1]124 = $CF_3CHClF$
[2]114a = $CF_3CCl_2F$

Example 2

Chlorination Using 6% $LaCl_3$/Acid Washed Carbon

The general chlorination procedure described above was followed. A solution of $LaCl_3 \cdot 6H_2O$ (3.46 g) in water (56 mL) was poured over 40 g of HCl-washed carbon. The resulting mixture was allowed to stand at room temperature for 1 hour with occasional stirring and was then placed in a vacuum oven at 120° C. for 18 hours to remove the water. A sample of this catalyst (14.6 g, 30 mL) was placed in the reactor and heated under a nitrogen flow to 350° C. over 1.5 hours. The temperature was reduced to 250° C. and the flows of chlorine and HCFC-124 started. Samples were taken at various times. The molar ratio of chlorine to HCFC-124 was 2:1 for all the samples. The contact time was 30 seconds for all the samples. The reactor effluent was analyzed as described above. The results are shown in Table 2.

TABLE 2

| Time (hr) | Temp. (°C.) | %124 | %114a |
|---|---|---|---|
| 2.0 | 250 | 55.7 | 44.2 |
| 2.5 | 275 | 22.4 | 77.6 |
| 3.5 | 300 | 3.3 | 96.6 |

Comparative Example A

Chlorination Using HCl-Washed Silicon Carbide

The general chlorination procedure described above was followed. A dried, acid-washed silicon carbide catalyst (48.8 g, 30 mL of 14×20 mesh (about 1.4×0.84 mm) granules was placed in the reactor and heated under a nitrogen flow to 275° C. The flows of chlorine and HCFC-124 were then started. Samples were taken at various times. The molar ratio of chlorine to HCFC-124 was 2:1 for all the samples. The contact time was 30 seconds for all the samples. The reactor effluent was analyzed as described above. The results are shown in Table A.

TABLE A

| Time (hr) | Temp. (°C.) | %124 | %114a |
|---|---|---|---|
| 1.0 | 275 | 95.5 | 4.4 |
| 1.5 | 300 | 91.1 | 8.9 |
| 2.5 | 325 | 77.3 | 22.7 |
| 3.5 | 350 | 53.2 | 46.8 |
| 4.0 | 375 | 22.0 | 77.8 |
| 5.0 | 400 | 3.4 | 96.1 |

Minor amounts of other products including $CClF_2CF_3$ and $CF_3CCl_3$ were also found.

Comparative Example B

Chlorination Using Calcined Shot Coke

The general chlorination procedure described above was followed. Conoco shot coke (31.0 g, 30 mL of 10×20 mesh (about 2.0×0.84 mm) granules), a highly fused petroleum coke with a surface area of 0.5 $m^2$/g was placed in a reactor and heated to 275° C.; and the flow of chlorine started. After a half hour, the flow of HCFC-124 was also started. Samples were taken at various times. The molar ratio of chlorine to HCFC-124 was 2:1 for all the samples. The contact time was 30 seconds. The reactor effluent was analyzed as described above. The results are shown in Table B.

TABLE B

| Time (hr) | Temp. (°C.) | %124 | %114a |
|---|---|---|---|
| 5.0 | 275 | 94.9 | 5.1 |
| 8.0 | 300 | 89.2 | 10.6 |
| 10.0 | 325 | 77.3 | 22.4 |
| 12.0 | 350 | 58.5 | 41.1 |
| 13.0 | 375 | 28.8 | 70.9 |
| 14.0 | 400 | 4.5 | 95.4 |

Comparative Example C

Chlorination Using Inconel® Chips

The general chlorination procedure described above was followed. Inconel® nickel alloy chips (139 g, mL) were placed in the reactor and heated under a nitrogen flow to 250° C. The flows of chlorine and HCFC-124 (97.8% pure) were then started. The molar ratio of chlorine to HCFC-124 was 2:1 for all the samples. The contact time was 30 seconds for all the samples. The reactor effluent was analyzed as described above. The results are shown in Table C.

TABLE C

| Time (hr) | Temp. (°C.) | %124 | %114a |
|---|---|---|---|
| 0 | FEED | 97.8 | 2.0 |
| 3.0 | 250 | 97.7 | 2.0 |
| 5.0 | 275 | 96.8 | 3.2 |
| 6.0 | 300 | 93.5 | 6.5 |
| 7.0 | 325 | 84.0 | 16.0 |
| 8.0 | 350 | 62.9 | 37.0 |

General Procedure for Hydrogenolysis

A 6" (about 15.2 cm)×½" (about 1.3 cm) O.D. Hastelloy™ C nickel alloy reactor was charged with the catalyst (5.0 g) for hydrogenolysis. The reactor contents were heated to a temperature of 175° C. over a period of five hours, during which time an equimolar flow, 10 cc/min each, of nitrogen and hydrogen was passed through the reactor. At the end of this five hour period, nitrogen flow was stopped, the hydrogen flow increased to 20 cc/min, the reactor temperature raised to 275° C. over a 2.5 hour period and maintained at this temperature for an additional 16 hours. After this period, the reactor temperature was decreased to the desired operating temperature for hydrogenolysis.

Example 3

Hydrogenolysis of CFC-114a Using 0.5% Pd on HCl/HF-washed Carbon

A commercially available carbon (500 g, 6×16 mesh (about 3.4×1.2 mm) granules) was soaked for 120 hours with gentle stirring in 1M HCl. The carbon granules were collected on a fritted glass funnel and washed with deionized water (422 L) until the washings were chloride free when tested with silver nitrate. Finally the carbon granules were dried at 120° C. for 60 hours followed by calcination at 300° C. in air to obtain 8.8 g of dried calcined granules. HCl-washed carbon (225 g, 6×16 mesh (about 3.4×1.2 mm) granules) prepared as described above was soaked for 48 hours at room temperature with occasional stirring in 1M HF (3 L) in a plastic jug. The carbon granules were then placed in a 4 L plastic beaker on a steam bath and washed with deionized water (3 L portions, at about 50° C.) until the washings had a pH greater than 4.0 (114 L). Finally the carbon granules were dried at 150° C. for 60 hours in air followed by calcination at 330° C. in air for three hours to obtain 216.6 g of dried calcined granules. A portion of (100 g) of the HCl/HF-washed carbon prepared as described above was added to a solution of palladium chloride (0.84 g) in conc. hydrochloric acid (2.0 mL) and deionized water (160 mL). The slurry was then stirred occasionally at room temperature for two hours. It was then dried with frequent stirring at 150° C. for 18 hours in air to obtain 101.7 g of 0.5% Pd on carbon. A sample (97.4 g) of the above dried catalyst was placed in a quartz boat under a helium flow of 100 cc/min. for 15 minutes at room temperature. The catalyst was then heated as follows: 150° C./1 hr./helium (100 cc/min.); 150° C./1 hr./helium (100 cc/min.)-hydrogen (100 cc/min.); 300° C./8 hr./helium (100 cc/min.)-hydrogen (100 cc/min.). The hydrogen flow was stopped; the catalyst was maintained at 300° C. in helium (100 cc/min.) for ½ hr. followed by cooling in helium. Finally the catalyst was passivated with 1.5% oxygen in nitrogen at room temperature for ½ hour.

The catalyst was used for the hydrogenolysis of CFC-114a using the general procedure for hydrogenolysis described above. The CFC-114a hydrogenolysis was done under the following conditions: temperature=150° C., pressure =atmospheric, $[H_2]/[CFC-114]=2$, total flow=30 cc/min. The products leaving the reactor were analyzed on line using a gas chromatograph. The column consisted of a 20' (about 6.1 m)×⅛" (about 3.2 mm) s/s tube containing Krytox™ perfluorinated polyether on an inert support. Helium was used as the carrier gas. The product analyses, reported in area %, are shown in Table 3. The first numbers in the table are for a run time of about 5.5 hours, and the second numbers represent analysis for a run time of about 26 hours.

TABLE 3

| | $CF_3CCl_2F \rightarrow CF_3CHClF + CF_3CH_2F$ | | | |
|---|---|---|---|---|
| %114a Conv. | % Sel. to 124 | % Sel. to 134a[1] | % Sel. to 143a[2] | % Sel. to 124 + 134a |
| 51.9 | 16.8 | 81.6 | 1.6 | 98.4 |
| 52.9 | 11.0 | 87.0 | 2.0 | 98.0 |

[1]134a = $CF_3CH_2F$
[2]143a = $CF_3CH_3$

Comparative Example D

The catalyst prepared as in Example 3 was used for the hydrogenolysis of HCFC-124 using the general procedure for hydrogenolysis described above. The HCFC-124 hydrogenolysis was done under the following conditions: temperature=250° C. pressure=atmospheric, $[H_2]/[HCFC-124]=1$, total flow=20 cc/min. The products leaving the reactor were analyzed on line using the gas chromatograph described in Example 3. The product analyses, reported in area %, are shown in Table D. The first numbers in the table are for a run time of about 5.5 hours, and the second numbers represent analyses for a run time of about 26 hours.

TABLE D

| | $CF_3CHClF \rightarrow CF_3CH_2F$ | |
|---|---|---|
| %124 Conv. | % Sel. to 134a | % Sel. to 143a |
| 50.5 | 94.3 | 6.7 |
| 50.7 | 95.5 | 4.5 |

Comparison of the results in Table 3 and Table D show that for approximately the same degree of conversion of CFC-114a and HCFC-124 the hydrogenolysis temperature is 100° C. less for CFC-114a (150° C. vs. 250° C.). Loss of HF from the product HFC-134a results in formation of HFC-143a. HF as well as the higher temperature required for HCFC-124 hydrogenolysis can accelerate catalyst decay.

The examples serve to illustrate particular embodiments of the invention. Other embodiments will become apparent to those skilled in the art from a consideration of the specification or practice of the invention disclosed herein. It is understood that modifications and variations may be practiced without departing from the spirit and scope of the novel concepts of this invention. It is further understood that the invention is not confined to the particular formulations and examples herein illustrated, but it embraces such modified forms thereof as come within the scope of the following claims.

What is claimed is:

1. A process for producing 1,1,1,2-tetrafluoroethane from 2-chloro-1,1,1,2-tetrafluoroethane comprising the steps of: contacting a gaseous mixture containing said 2-chloro-1,1,1,2-tetrafluoroethane and chlorine with a chlorination catalyst at a temperature of from about 225° C. to about 450° C. to produce 2,2-dichloro-1,1,1,2-tetrafluroethane, wherein the chlorination catalyst is selected from the group consisting of carbon catalysts; and reacting said 2,2-dichloro-1,1,1,2-tetrafluroethane with hydrogen in the presence of a carbon-supported precious metal catalyst at a temperature of from about 100° C. to 250° C. to produce 1,1,1,2-tetrafluoroethane.

2. The process of claim 1 wherein the chlorination catalyst consists essentially of carbon.

3. The process of claim 2 wherein the carbon is acid-washed.

4. The process of claim 3 wherein the ash content of the carbon is about 0.5 percent by weight, or less.

5. The process of claim 1 or claim 4 wherein the chlorination catalyst is an activated carbon catalyst.

6. A process for producing 1,1,1,2-tetrafluoroethane from 2-chloro-1,1,1,2-tetrafluroethane comprising the steps of: contacting a gaseous mixture containing said 2-chloro-1,1,1,2-tetrafluoroethane and chlorine with chlorination catalyst at a temperature of from about 225° C. to about 450° C. to produce 2,2-dichloro-1,1,1,2-tetrafluroethane, wherein the chlorination catalyst is selected from the group consisting of catalysts of metal halide supported on carbon wherein the metal halide is a chloride and/or fluoride of a metal selected from the group consisting of lanthanum, zinc, copper, chromium, ruthenium, rhodium, platinum, and mixtures thereof; and reacting said 2,2-dichloro-1,1,1-tetrafluroethane with hydrogen in the presence of a carbon-supported precious metal catalyst at a temperature of from about 100° C. to 250° C. to produce 1,1,1,2-tetrafloroethane.

7. The process of claim 6 wherein the metal halide is lanthanum chloride and/or fluoride.

8. The process of claim 6 wherein the metal halide is a zinc chloride and/or fluoride.

9. The process of claim 6 wherein the metal halide is a copper chloride and/or fluoride.

10. The process of claim 6 wherein the metal halide is a chromium chloride and/or fluoride.

11. The process of claim 6 wherein the metal halide is a ruthenium chloride and/or fluoride.

12. The process of claim 6 wherein the metal halide is a rhodium chloride and/or fluoride.

13. The process of claim 6 wherein the metal halide is a platinum chloride and/or fluoride.

14. The process of claim 6, claim 7, claim 8, claim 9, claim 10, claim 11, claim 12, or claim 13 wherein the carbon is acid-washed.

15. The process of claim 1 wherein the chlorination temperature is from about 250° C. to 400° C.

16. The process of claim 1 wherein the mole ratio of chlorine to the organic starting material is between about 0.5:1 and 10:1.

17. A process for the manufacture of $CF_3CH_2F$ by reacting $CF_3CCl_2F$ with hydrogen wherein $CF_3CHClF$ is produced as a by-product, characterized by the steps of: contacting a gaseous mixture containing chlorine and said by-product $CF_3CHClF$ with a catalyst at a temperature of from about 225° C. to 450° C. to produce $CF_3CCl_2F$, wherein said catalyst is selected from the group consisting of carbon catalysts and catalysts of metal halide supported on carbon wherein the metal halide is a chloride and/or fluoride of a metal selected from the group consisting of lanthanum, zinc, copper, chromium, ruthenium, rhodium, platinum, and mixtures thereof; recycling the $CF_3CCl_2F$ produced by said chlorination for reaction with hydrogen; and reacting $CF_3CCl_2F$ with hydrogen in the presence of a carbon-supported precious metal catalyst at a temperature of from about 100° C. to 250° C.

18. The process of claim 6 wherein the chlorination temperature is from about 250° C. to 400° C.

19. The process of claim 6 wherein the mole ratio of chlorine to the organic starting material is between about 0.5:1 and 10:1.

* * * * *